(12) United States Patent
Bandyopadhyay et al.

(10) Patent No.: US 6,670,384 B2
(45) Date of Patent: Dec. 30, 2003

(54) METHODS OF ADMINISTERING EPOTHILONE ANALOGS FOR THE TREATMENT OF CANCER

(75) Inventors: Rebanta Bandyopadhyay, Portage, MI (US); Timothy M. Malloy, Yardley, PA (US); Andrea Panaggio, West Windsor, NJ (US); Krishnaswamy Srinivas Raghavan, Cranbury, NJ (US); Sailesh Amilal Varia, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/055,653

(22) Filed: Jan. 23, 2002

(65) Prior Publication Data

US 2002/0169190 A1 Nov. 14, 2002

Related U.S. Application Data

(60) Provisional application No. 60/264,228, filed on Jan. 25, 2001, and provisional application No. 60/290,008, filed on May 11, 2001.

(51) Int. Cl.$^7$ .............................................. A61K 31/365
(52) U.S. Cl. ........................................ 514/365; 514/183
(58) Field of Search ................................. 514/365, 183

(56) References Cited

U.S. PATENT DOCUMENTS

| | | | |
|---|---|---|---|
| 6,194,181 B1 | 2/2001 | Hofmann et al. | |
| 6,204,388 B1 | 3/2001 | Danishefsky et al. | |
| 6,211,412 B1 | 4/2001 | Georg et al. | |
| 6,387,927 B1 * | 5/2002 | Altmann et al. | 514/311 |
| 6,399,638 B1 * | 6/2002 | Vite et al. | 514/366 |
| 2002/0045609 A1 * | 4/2002 | Ashley et al. | 514/183 |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | WO99/02514 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |

OTHER PUBLICATIONS

U.S. patent application Ser. No. 08/856,533, Nicolaou et al., filed May 14, 1997.

U.S. patent application Ser. No. 08/923,869, Nicolaou et al., filed Sep. 4, 1997.

U.S. patent application Ser. No. 60/032,864, Nicolaou et al., filed Dec. 13, 1996.

Balog, A., et al., "Total Synthesis of (–)–Epothilone A", *Angew. Chem. Int. Ed. Engl.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujisawa, T., et al., "Deoxygenation of Epoxides to Olefins with $FeCl_3$—2–BuLi System", *Chem. Lett.*, 883–886 (1974).

(List continued on next page.)

Primary Examiner—James H Reamer
(74) Attorney, Agent, or Firm—Rena Patel

(57) ABSTRACT

A process for formulating certain epothilone analogs for parenteral administration is disclosed wherein the analog is dissolved in a mixture of at least 50% by volume tertiary-butanol in water, the mixture is lyophilized, the resulting lyophilized product is packaged in one vial with a sufficient amount of solvent comprising anhydrous ethanol and a suitable nonionic surfactant in a second vial. All steps are carried out with protection from light. In use, the contents of the second or diluent vial are added to the lyophilized product and mixed to constitute the epothilone analog and the resulting solution is diluted with a suitable diluent to produce a solution for intravenous injection containing the epothilone analog in a concentration of from about 0.1 mg/mL to about 0.9 mg/mL. A preferred surfactant is polyethoxylated castor oil and a preferred diluent is Lactated Ringer's Injection.

105 Claims, No Drawings

OTHER PUBLICATIONS

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

Gladysz, J. A., et al., "Deoxygenation of Epoxides by Metal Atom Cocondensation", *J. Org. Chem.*, vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to olefins with Low Valent Titanium", *J. Org. Chem.*, vol. 40, No. 17, 2555–2556 (1975).

McMurry, J. E., et al., "Some Deoxygenation Reactions with Low–Valent Titanium ($TiCl_3/LiAlH_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et. al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to epothilone A and Its Analogues", *J. Am. Chem. Soc.*, vol. 119, No. 34, 7960–7973 (1997).

Nicolaou, K. C., et al., "Total Synthesis of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5/NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1/2, 166–168 (1997).

Bollag, D., et al., "Epothilone, A New Structural Class of Microtubule Stabilizer", Abstract, *Proc. Am. Assoc. Cancer. Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A; Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Synthesis of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, L., et al., "Total Synthesis of Epothilone E and Related Side–chain Modified Analogues Via A Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)-Epothilone A", *Chem. Eur. J.*, vol. 5, No. 9, 2483–2491 (1999).

Schinzer, D., et al., "Syntheses of (–)-Epothilone B", *Chem. Eur. J.*, vol. 5, No. 9, 2492–2500 (1999).

Nicolaou, K. C., et al., "Synthesis and Biological Properties of C12,13–Cyclopropylepothilone A and Related Epothilones", *Chemistry & Biology*, vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84–87 (1998).

Nicolaou et al., "Total Synthesis of Oxazole– and Cyclopropane–Containing Epothiloe B Analogues by the Macrolactonization Approach", Chemistry, European Journal, vol. 3, No. 12, 1971–1986 (1997).

Nicolaou et al., "Chemical Biology of Epothilones", Angew. Chem. Int. Ed., 37, 2014–2045 (1988).

* cited by examiner

METHODS OF ADMINISTERING EPOTHILONE ANALOGS FOR THE TREATMENT OF CANCER

CROSS-REFERENCE TO RELATED APPLICATIONS

This application claims priority from provisional application serial No. 60/264,228, filed Jan. 25, 2001 and 60/290,008, filed May 11, 2001, both of which are incorporated herein by reference in their entirety.

FIELD OF THE INVENTION

The present invention relates to methods of administration for parenteral and oral compositions of certain epothilone analogs that are characterized by enhanced clinical efficacy.

BACKGROUND OF THE INVENTION

Epothilones are macrolide compounds having utility in the pharmaceutical field. For example, Epothilones A and B having the structures:

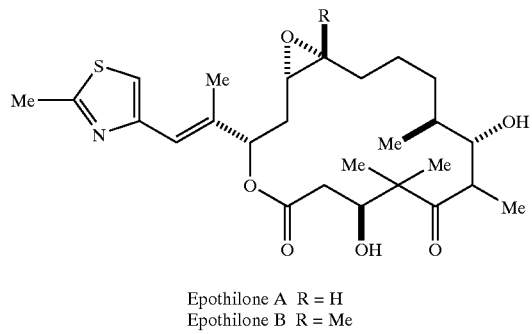

Epothilone A R = H
Epothilone B R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle et al., *Angew. Chem. Int. Ed. Engl.*, Vol. 35, No.13/14, 1567–1569 (1996); WO 93/10121 published May 27, 1993; and WO 97/19086 published May 29, 1997.

Derivatives and analogs of Epothilones A and B have been synthesized and may be used to treat a variety of cancers and other abnormal proliferative diseases. Such analogs are disclosed in Hofle et al., Id.; Nicolaou et al., *Angew Chem. Int. Ed. Engl.*, Vol. 36, No. 19, 2097–2103 (1997); and Su et al., *Angew Chem. Int. Ed. Engl.*, Vol. 36, No. 19, 2093–2097 (1997).

Analogs of the epothilones that have been found to have advantageous activity are represented by formula I:

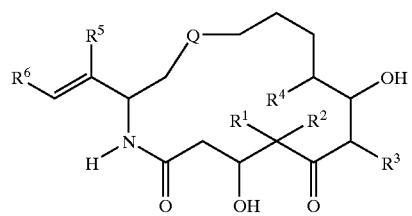

I wherein the various symbols are as defined below. While these compounds possess significant therapeutic properties, they also present difficulties to those skilled in the art of pharmaceutical compounding, as a result of certain properties, as will be detailed hereinbelow. In accordance with the present invention, a formulation has been found whereby the epothilone analogs described above can be safely dispensed and administered via injection, without appreciable loss of potency.

Furthermore, many anti-cancer drugs have toxicity concerns. Indeed, the therapeutic profile of many potent antitumor drugs is poor as a result of toxicity. Therefore, there is also a need for methods of administration and dosing schedules that reduce or avoid the toxicity associated with antitumor agents. The methods can allow exploitation of potent antitumor agents that would otherwise not be used clinically.

SUMMARY OF THE INVENTION

The invention encompasses a novel dosing schedule for epothilone compounds, which schedule is useful in treating patients having solid tumors, particularly advanced solid tumors. Further, the methods of the invention can be used to treat and/or prevent metastatic as well as primary tumors. In one embodiment, the invention encompasses the treatment of patients that have previously received either or both radiation therapy and chemotherapy for solid tumors. It has also been found that the epothilone compounds of the invention particularly the preferred compound, [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, can be used to treat tumors refactory to radiation therapy or chemotherapy. The methods of the invention are useful against cancer cells, and thus, tumors, that are naturally or become insensitive to paclitaxel.

In one embodiment, the dosing schedule of the invention comprises the weekly administration of an epothilone compound of the invention preferably as a one (1) hour infusion weekly on a continuous basis. In another embodiment, the administration is made weekly for a three week cycle. The dose range for weekly infusion is from 1 mg/m$^2$ to 30 mg/m$^2$ and more preferably 1 mg/m$^2$ to 25 mg/m$^2$. In another embodiment, the dosing schedule includes both oral and intravenous administration of the same epothilone compound. For example, the weekly infusion can be followed or preceded by an oral administration of 20 mg/m$^2$ or greater. In a specific embodiment, the administration regimen includes a three (3) week cycle of intravenous infusion once per week for about one (1) hour followed by or preceded by an oral dose administered one or more times in the week before the first intravenous administration of a cycle or the week after the last intravenous administration of a cycle. Other protocols are also encompassed within the present invention including but not limited to:

(a) a daily dosing for 5 to 10 days followed by at least 3 days of no dosing;
(b) weekly dosing for two to ten weeks followed by at least one week of no dosing; and
(c) dosing once every three weeks followed by at least one week of no dosing.

The invention also contemplates the use of $H_1$ and $H_2$ antihistamines before, after and/or before and after a cycle of epothilone administration. Similarly, the invention encompasses the use of other chemotherapeutics, particularly anti-tumor agents, with epothilone cycle alone, or with the $H_1$ and $H_2$ blockers and the epothilones.

In another embodiment, the epothilone dosing schedule is used after the standard regimen of paclitaxel.

As discussed herein a wide variety of cancers are encompassed by the methods of the present invention. In a preferred embodiment, the methods of the invention are for the treatment of solid tumors including but not limited to breast, head and neck, sarcoma, colorectal, UPT, melanoma, oesophagus, renal, cervix, thyroid, anal, ovarian, and colon.

The methods and compositions of the present invention describes a formulation and the preparation thereof for epothilone analogs represented by formula I:

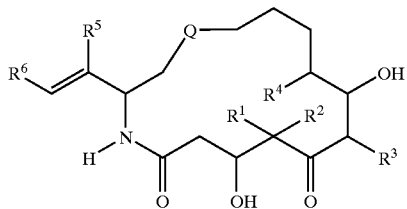

wherein the various symbols are as defined below.

In one embodiment of the formulations of the present invention, the epothilone analog is initially solubilized with a mixture of tertiary-butanol and water and then lyophilized under optimized conditions. The lyophilized drug is reconstituted first with a mixture of a polyethoxylated castor oil surfactant and anhydrous ethanol, and thereafter diluted with Lactated Ringer's Injection to a concentration appropriate for administration.

DETAILED DESCRIPTION OF THE INVENTION

In an embodiment, the present invention provides an advantageous formulation for the administration of epothilone analogs represented by formula I:

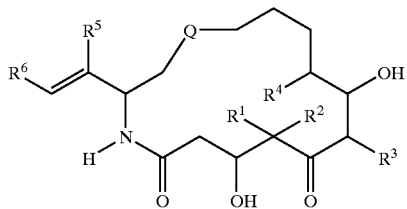

As used in formula I and throughout the specification, Q is selected from the group consisting of:

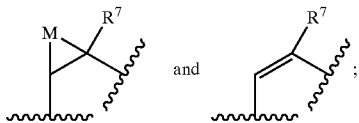

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$ and $R^{14}$ is, independently, selected from the group consisting of hydrogen, alkyl, substituted alkyl, aryl, substituted aryl and heterocyclo, and wherein $R^1$ and $R^2$ are alkyl, they can be joined to form cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$.

The following are definitions of various terms used herein to describe the present invention. These definitions apply to the terms as they are used throughout this specification, unless otherwise limited in specific instances, either individually or as part of a larger group.

The term "alkyl" refers to optionally substituted straight- or branched-chain saturated hydrocarbon groups having from 1 to about 20 carbon atoms, preferably from 1 to about 7 carbon atoms. The expression "lower alkyl" refers to optionally substituted alkyl groups having from 1 to about 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "halogen" or "halo" refers to fluorine, chlorine, bromine and iodine.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having from about 6 to about 12 carbon atoms in the ring portion, for example, phenyl, naphthyl, biphenyl and diphenyl groups, each of which may be substituted.

The term "aralkyl" refers to an aryl group bonded to a larger entity through an alkyl group, for example, a benzyl group.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula I in an equivalent amount of the acid in a medium in which the salt precipitates or in an aqueous medium followed by evaporation.

In addition, zwitterions ("inner salts") can be formed and are included within the term salts as used herein.

A particularly preferred epothilone analog within those represented by formula I is [1S-[1R*,3R*(E),7R*,10S*, 11R*, 12R*,16S*,]]-7,11-Dihydroxy-8,8,10,12,16-pentamethyl-3-[1-methyl-2-(2-methyl-4-thiazolyl)ethenyl]-4-aza-7-oxabicyclo[14.1.0]heptadecane-5,9-dione represented by formula II:

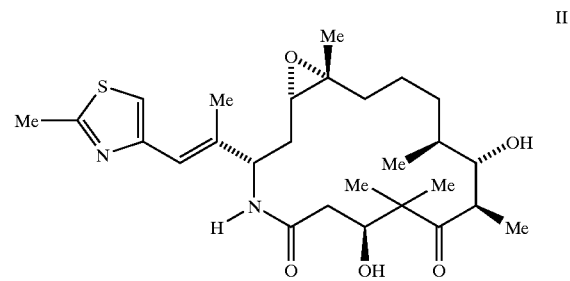

The compounds represented by formulae I and II above, also referred to herein as "the epothilone compounds of the invention," and their preparation are described in U.S. patent application Ser. No. 09/170,582, filed Oct. 13, 1998, and U.S. patent application Ser. No. 09/280,191, filed Mar. 29, 1999, the disclosure of which is incorporated herein by reference. The compounds represented by formulae I and II above may exist as multiple optical, geometric, and stereoisomers. While the compounds shown herein are depicted for one optical orientation, included within the present invention are all isomers and mixtures thereof.

The compounds represented by formulae I and II above are microtubule-stabilizing agents. They are thus useful in the treatment of a variety of cancers and other proliferative diseases including, but not limited to, the following:

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The compounds represented by formulae I and II are useful for treating patients who have been previously treated for cancer, as well as those who have not previously been treated for cancer. Indeed, the methods and compositions of this invention can be used in first-line and second-line cancer treatments. Furthermore, the compounds represented by formulae I and II are useful for treating refractory cancers.

The compounds represented by formulae I and II above will also inhibit angiogenesis, thereby affecting the growth of tumors and providing treatment of tumors and tumor-related disorders. Such anti-angiogenesis properties of the compounds represented by formulae I and II will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds represented by formulae I and II will induce or inhibit apoptosis, a physiological cell death process critical for normal development and homeostasis. Alterations of apoptotic pathways contribute to the pathogenesis of a variety of human diseases. Compounds represented by formulae I and II, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Each of the compounds represented by formulae I and II may also be formulated or co-administered with other therapeutic agents that are selected for their particular usefulness in administering therapies associates with the aforementioned conditions. For example, each of the compounds of formulae I and II may be formulated with agents to prevent nausea, hypersensitivity, and gastric irritation, such as antiemetics, and $H_1$ and $H_2$ antihistamines. The above therapeutic agents, when employed in combination with the compound of formulae I or II, may be used in those amounts indicated in the Physicians' Desk Reference (PDR) or as otherwise determined by one of ordinary skill in the art.

Furthermore, compounds of formulae I or II may be administered in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g., S phase, than the present compounds of formula I and II which exert their effects at the $G_2$-M phase. Example classes of anti-cancer and cytotoxic agents include, but are not limited to, alkylating agents, such as nitorgen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®); plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. Compounds represented by formulae I and II may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: cyclin dependent kinase inhibitors as found in WO 99/24416; and prenyl-protein transferase inhibitors as found in WO 97/30992 and WO 98/54966.

The compounds may also be administered with or after anti-cancer and cytotoxic agents that are neurotoxic, i.e., poisonous to the nervous system.

Without being bound by any theory regarding mechanism or morphology, the compounds represented by formulae I and II may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzeimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The compounds represented by formulae I and II, particularly the latter, are difficult to formulate in that they possess very low solubility in aqueous media, rapidly degrade in contact with aqueous media, are sensitive to low pH when in solution, are light sensitive, are "Class D" cytotoxic, and have exceptionally poor wetting characteristics. Any one or two of these characteristics might be compensated for in compounding a pharmaceutical formulation for intravenous administration, but the combination of all of them presents a formidable challenge to the pharmaceutical compounding chemist. Given the constraint that materials to be utilized in compounding an intravenous formulation must be approved for intravenous administration, the formulation provided in accordance with the present invention unexpectedly was found to be suitable for overcoming the properties of the subject epothilone analogs, as noted above, that make them difficult to formulate. Initially, because of the fact that the subject epothilone analogs are poorly soluble in aqueous media and, in fact, rapidly degrade in contact therewith, it was decided that they should be formulated in lyophilized form.

It has been found that a suitable media to form a solution of the subject compounds for lyophilization is a mixture of tertiary-butanol and water for injection. This mixture must be at least about 50% v/v, preferably from about 50% to about 80% v/v tertiary butanol to prevent degradation of the subject epothilone analogs. Further, due to the exceptionally poor wetting characteristics of the subject epothilone analogs, the initial solution must be effected utilizing a mixture of at least about 60% v/v, preferably from about 60% to about 95% v/v, tertiary butanol and water. Once the solution is made, the requisite amount of water or tertiary-butanol-water mixture can be added to achieve the final concentration for lyophilization as stated above.

It has unexpectedly been found that the stability of the subject epothilone analogs can be significantly enhanced by carrying out the preparation of the solution at a temperature below ambient, preferably from about 5 EC to about 15 EC, more preferably about 5 EC. Further, both the process of forming the solution and subsequent lyophilization are to be carried out in vessels such that the epothilone analogs are protected from exposure to light. It is also beneficial to carry out the lyophilization in comparatively small batches so that the epothilone analogs are exposed to an aqueous medium for a minimum amount of time.

The primary drying stage of lyophilization of the solution formed as described above is carried out at temperatures from about –10 EC to about –40 EC, preferably about –25 EC, under high vacuum, ie., from about 50 millitorr to about 300 millitorr, preferably about 200 millitorr, for an extended period, i.e., from about 24 hours to about 96 hours, preferably about 48 hours. Lyophilization in this temperature range produces an amorphous product which is desirable for an intravenous preparation. Those of ordinary skill in the art will appreciate that conventional procedures, such as powder X-ray diffraction, can be utilized to confirm the amorphous nature of the lyophilized product.

The residual solvents in the product are removed by a secondary drying stage that is carried out at comparatively low temperatures, i.e., from about 10 EC to about 30 EC, preferably about 25 EC, under high vacuum, i.e., from about 50 millitorr to about 300 millitorr, preferably about 150 millitorr for an extended period, i.e., from about 24 hours to about 96 hours, preferably about 48 hours.

It has unexpectedly been found that the stability of lyophilized epothilone analogs described herein are not enhanced by excipients commonly utilized for such purposes, such as lactose, mannitol, dextran and the like. Certain of these excipients may actually have a negative effect on the stability of the lyophilized product (lyophile). Hence, the epothilone analogs formulated in accordance with the present invention are lyophilized neat, i.e., without any excipient.

The lyophilized epothilone analogs represented by formulae I and II are reconstituted with a mixture of equal parts by volume of Dehydrated Alcohol, USP and a nonionic surfactant, preferably a polyoxyethylated castor oil surfactant available from GAF Corporation, Mount Olive, N.J., under the trademark, Cremophor EL. The lyophilized product and vehicle for reconstitution are packaged separately in appropriately light-protected vials. To minimize the amount of surfactant in the reconstituted solution, only a sufficient amount of the vehicle is provided to form a solution having a concentration of about 2 mg/mL to about 4 mg/mL of the epothilone analog. Once dissolution of the drug is achieved, the resulting solution is further diluted prior to injection with a suitable parenteral diluent. Such diluents are well known to those of ordinary skill in the art. These diluents are generally available in clinical facilities. It is, however, within the scope of the present invention to package the subject epothilone analogs with a third vial containing sufficient parenteral diluent to prepare the final concentration for administration. A preferred diluent is Lactated Ringer's Injection. The final concentration for administration would preferably contain from about 0.1 mg/mL to about 0.9 mg/mL of the epothilone analog.

The final dilution of the reconstituted epothilone analog in the formulation of the invention may be carried out with other preparations having similar utility, for example, 5% Dextrose Injection, Lactated Ringer's and Dextrose Injection, Sterile Water for Injection, and the like. However, because of its narrow pH range, pH 6.0 to 7.5, Lactated Ringer's Injection is preferred. Per 100 mL, Lactated Ringer's Injection contains Sodium Chloride USP 0.6 g, Sodium Lactate 0.31 g, Potassium chloride USP 0.03 g and Calcium Chloride-2H20 USP 0.02 g. The osmolarity is 275 mOsmol/L, which is very close to isotonicity.

The constituted preparation according to the present invention, i.e., the solution of the epothilone analog in the alcohol-surfactant vehicle, can be stored for up to about 24 hours before being further diluted for administration. It has been found that the incidence of allergic reactions encountered due to the presence of the surfactant in the formulation is minimized by keeping its concentration at the minimum necessary to effect solution of the epothilone analog. Further, the incidence of such reactions is about the same as has been experienced with other parenterally administered pharmaceuticals containing it, such as cyclosporine. This observed level of allergic reaction with the present formulation is significantly lower that has been experienced with certain other oncology agents, such as Paclitaxel.

The present invention is also directed to methods of treating cancer and other hyperproliferative diseases in patients comprising administering to the patient a therapeutically effective amount of one or more compounds represented by formulae I and II. The compounds of formula I and II may be administered intravenously or orally, preferably both orally and intravenously. Preferably, the compounds of formulae I and II are administered with one or more additional agents to prevent nausea, hypersennsitivity, or gastric irritation such as an anti-emetic or an $H_1$ or $H_2$ antihistamine.

The amount of a compound represented by formulae I and II administered by each IV infusion, or orally, or both may be determined by one of ordinary skill in the art, and includes exemplary dosage amounts for a human of from about 0.01 mg/kg/day to about 200 mg/kg/day, which may be administered in a single dose or in the form of individual divided doses, such as from 1 to about 4 times per day. Preferably, the compounds are administered in a dosage of less than about 100 mg/kg/day, and more preferably less than about 25 mg/kg/day in a single dose or in about 2 to about 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

Typically the compounds of formulae I and II are administered until the patient shows a response, for example, a reduction in tumor size, or until dose limiting toxicity is reached. One or ordinary skill in the art will readily know when a patient shows a response or when dose limiting toxicity is reached. The common dose limiting toxicities associated with compounds of formulae I and II include, but are not limited to, fatigue, arthralgia/myalgia, anorexia, hypersensitivity, neutropenia, thrombocytopenia, and neurotoxicity.

When administered intravenously, the compounds of formulae I and II are preferably administered using the formulations of the invention. Generally, the compounds of Formulae I and II are administered by IV infusion over a period of from about 10 minutes to about 3 hours, preferably about 30 minutes to about 2 hours, more preferably about 45 minutes to 90 minutes, and most preferably about 1 hour. Typically, the compounds are administered intravenously in a dose of from about 0.5 mg/m$^2$ to 65 mg/m$^2$, preferably about 1 mg/m$^2$ to 50 mg/m$^2$, more preferably about 2.5 mg/m$^2$ to 30 mg/m$^2$, and most preferably about 25 mg/m$^2$.

One of ordinary skill in the art would readily know how to convert doses from mg/kg to mg/m2 given either or both the height and or weight of the patient (See, e.g., http://www.fda.gov/cder/cancer/animalframe.htm).

When administered orally the compounds of formulae I and II are preferably administered in combination with a pharmaceutically acceptable acid neutralizing buffer. The buffer neutralizes acid in the stomach of the patient so that the rate of decomposition of the compounds of formulae I and II is sufficiently decreased so that they remain in the gastrointestinal tract for sufficient time to be absorbed. The compounds of formulae I and II may also be administered with an anti-acid such as hydroxides of aluminum and magnesium; carbonates, such as sodium carbonate and calcium carbonate; silicates; and phosphates to neutralize the acid in the stomach before during or after administration of the compounds of formulae I and II.

As used herein, the term "pharmaceutically acceptable acid neutralizing buffer" refers to a combination of a pharmaceutically acceptable non-toxic acid and a pharmaceutically acceptable non-toxic salt of an acid that when added to a solution provides a solution that is more resistant to change of pH, compared to a solution without the buffer, when acid or alkali is added to the solution. The term "pharmaceutically acceptable acid neutralizing buffer" also includes compounds, such as basic compounds, that when added to an acidic solution neutralizes the acid and increases the pH of the solution.

In one embodiment of the invention, the compounds of formulae I and II and the pharmaceutically acceptable acid neutralizing buffer are provided in a single oral dosage form and are administered simultaneously. The single composition comprising the combination of the compounds of formulae I and II may be administered as a solid oral dosage form (e.g., a tablet, capsule, or powder) or a liquid oral dosage form (e.g., a solution, suspension, or elixir). The solution or suspension can be constituted just prior to administration using the appropriate solvents or cosolvents to dissolve the epothilone and the buffer components.

For example, the compounds of formulae I and II and the pharmaceutically acceptable acid neutralizing buffer may be orally administered simultaneously as a solution of the epothilone of formula (I) or (II) dissolved in a liquid comprising propylene glycol:ethanol:phosphate buffer (for example at 1M, about pH 8) in a ratio of about 58:12:30, respectively.

The compounds of formulae I and II and the pharmaceutically acceptable acid neutralizing buffer can also be provided as separate distinct pharmaceutical compositions and administered separately. Each of which are administered as a solid oral dosage form or a liquid oral dosage form. When the compounds of formulae I and II and the pharmaceutically acceptable acid neutralizing buffer are administered separately, the pharmaceutically acceptable acid neutralizing buffer may be orally administered before, after, or both before and after the compounds of formulae I and II is administered. Preferably, the pharmaceutically acceptable acid neutralizing buffer is administered both before and after oral administration of the compounds of formulae I and II, in an amount sufficient to neutralize the stomach acid. When the pharmaceutically acceptable acid neutralizing buffer is administered before the compounds of formulae I and II it is administered within about 5 hours preferably within about 3 hours, more preferably within about 1 hour, and most preferably with about 10 minutes before the compounds of formulae I and II is administered. When the pharmaceutically acceptable acid neutralizing buffer is administered after the compounds of formulae I and II it is administered within about 5 hours, preferably within about 3 hours, more preferably within about 1 hour, and most preferably within about 10 minutes after the compounds of formulae I and II is administered.

The compounds of formulae I and II can also be administered as an enteric coated pill or capsule to delay release of the epothilone until after the pharmaceutically effective acid neutralizing buffer is administered. Enteric coated tablets and capsules are capsules coated with a substances that resist solution in a gastric fluid but disintegrate in the intestine.

Typically, the pharmaceutically acceptable acid neutralizing buffer is administered in an amount sufficient to deliver at least about 20 milliequivalents of acid neutralization capacity, preferably at least about 30 milliequivalents of acid neutralization capacity, more preferably at least about 40 milliequivalents of acid neutralization capacity, and most preferably at least about 50 milliequivalents of acid neutralization capacity. Typically, the pharmaceutically acceptable acid neutralizing buffer is administered as an aqueous solution having a pH of between about 5 to 9, preferably about 6 to 8.5, and more preferably about 7 to 8. Any pharmaceutically acceptable acid neutralizing buffer that provides a solution having a pH in the desired range may be used in the methods of the invention. Preferably, the pharmaceutically acceptable acid neutralizing buffer is a dibasic phosphate-monobasic phosphate buffer or a dibasic phosphate buffer-citric acid-citrate buffer.

For example, oral administration of the compounds of formulae I and II can involve first orally administering to the patient the pharmaceutically acceptable acid neutralizing buffer as about 150 mL of an aqueous solution comprising anhydrous dibasic sodium phosphate (about 0.2 M), sodium citrate dihydrate (about 0.07 M), and anhydrous citric acid (about 0.008 M) at a pH of about 7.4; followed by oral administration of the compounds of formulae I and II as a liquid dosage form in a propylene glycol:ethanol system having a ratio of about 80:20; followed by oral administration of another about 150 mL aqueous solution comprising anhydrous dibasic sodium phosphate (about 0.2 M), sodium citrate dihydrate (about 0.07 M), and anhydrous citric acid (about 0.008 M) at a pH of about 7.4.

As discussed above, the compounds of formulae I and II can be administered orally, intravenously, or both. In particular, the methods of the invention encompass dosing protocols such as once a day for 2 to 10 days, preferably every 3 to 9 days, more preferably every 4 to 8 days and most preferably every 5 days. In one embodiment there is a period of 3 days to 5 weeks, preferably 4 days to 4 weeks, more preferably 5 days to 3 weeks, and most preferably 1 week to 2 weeks, in between cycles where there is no treatment. In another embodiment the compounds of formulae I or II can be administered orally, intravenously, or both, once a day for 3 days, with a period of preferably 1 week to 3 weeks in between cycles where there is no treatment. In yet another embodiment the compounds of formulae I or II can be administered orally, intravenously, or both, once a day for 5 days, with a period of preferably 1 week to 3 weeks in between cycles where there is no treatment.

In one preferred embodiment the treatment cycle for administration of the compounds of formulae I or II is once daily for 5 consecutive days and the period between treatment cycles is from 2 to 10 days, preferably one week.

The compounds of formulae I and II can also be administered orally, intravenously, or both once every 1 to 10 weeks, preferably every 2 to 8 weeks, more preferably every 3 to 6 weeks, and even more preferably every 3 weeks.

In another method of the invention, the compounds of formulae I and II are administered in a 28 day cycle wherein the compound of formulae I and II are intravenously administered on days 1, 7, and 14 and orally administered on day 21. Alternatively, the compounds of formulae I and II are administered in a 28 day cycle wherein the compound of formulae I and II are orally administered on day 1 and intravenously administered on days 7, 14, and 28.

According to the methods of the invention, the compounds of formulae I and II are administered until the patient shows a response, for example, a reduction in tumor size, or until dose limiting toxicity is reached.

Many anti-cancer agents are neurotoxic, e.g., they are known to cause side effects of the central and peripheral nervous system. This invention further encompasses the use of compounds of formulae I and II in patients previously experiencing neurotoxicity with other anti-cancer agents. Although, the compounds of the invention may also cause neurotoxicity at certain doses, the methods herein can be used to reduce or avoid such toxicity.

EXAMPLES

The following non-limiting example serves to illustrate the practice of the present invention.

Example 1

IV Dosage Form

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0] heptadecane-5,9-dione, 9.86 g, was wetted/partially dissolved with 600 mL of a 9:1 mixture of tertiary butanol and Water for Injection USP which had been pre-cooled to 5 EC. Once the drug powder had become completely wetted, dissolution was completed by the addition of 600 mL of a 1:9 mixture of tertiary butanol and Water for Injection and 766 mL of a 1:1 mixture of tertiary butanol and Water for Injection which likewise had been pre-cooled to 5 EC thereby making the final solution a 1:1 mixture. The dissolution was carried out under protection from light.

The solution formed above was promptly lyophilized in a Virtis INOTOP lyophilizer at −16 EC under light protectant conditions over a period of 48 hours. The resultant lyophilized product (lyophile) was then further dried at 15 EC under high vacuum for 48 hours. No detectable degradation of the drug was observed during these procedures. The lyophile was packaged under sterile conditions into 30 mL vials, each containing 10 mg of drug and standard excess to allow for vial/needle/syringe loss.

The lyophile is reconstituted with 5.5 mL of a 1:1 volume mixture of Dehydrated Alcohol USP and Cremophor EL®, which typically will be supplied with the drug in a separate vial, to achieve a final drug concentration of 2 mg/mL. Once dissolution is effected by gently swirling the vial, the resultant solution is diluted to achieve a concentration of 0.2 mg/mL by the addition of 9 mL of Lactated Ringer's for Injection for each milliliter of constituted drug product.

Example 2

IV Administration of Compound II

A total of 24 cancer patients (12 male and 12 female) received compound II by IV administration to evaluate the maximum tolerated dose (MTD), the dose limiting toxicity (DLT), the pharmacokinitics and pharmacodynamics, and to evaluate the anti-tumor activity of compound II. The median age (range) of the patients was 57 (34–74). 5 patients had breast cancer, 5 patients had head and neck cancer, 2 patients had sarcoma, 2 patients had colorectal cancer, 2 patients had UPT cancer, 2 patients had melanoma, 2 patients had cancer of the esophagus, 1 patient had renal cancer, 1 patient had cervical cancer, 1 patient had thyroid cancer, and 1 patient had anal cancer. 21 patients had received prior chemotherapy (18 patients received neurotoxic agents and 18 patients received radiotherapy). The median number of prior chemotherapy lines including adjuvant (range) was 2 (1–3).

Patients were orally administered compound II on day 1 (for dose levels of 20 mg/m$^2$ and higher) followed by a 30 minute IV infusion of compound II every week starting on day 7. Patients were administered compound II at doses of 1, 2.5, 5, 10, 20, 25, and 30 mg/m$^2$. Patients were monitored during the course of treatment for dose limiting toxicity (DLT) The results of the study showed that compound II can be administered weekly at doses up to 30 mg/m$^2$ without severe toxicity being observed.

In a second study a total of 12 cancer patients (5 male and 7 female) were orally administered compound II on day 1 followed by a 30 minute IV infusion of compound II every week starting on day 7 at a dose of 25 mg/m$^2$ to evaluate neurotoxicity of compound II. The median age (range) of the patients was 51 (30–65). 4 patients had colorectal cancer, 3 patients had breast cancer, 2 patients had melanoma, 1 patient had renal cancer, 1 patient had sarcoma, and 1 patient had ovary cancer. 10 patients had received prior chemotherapy (6 patients received neurotoxic agents and 18 patients received radiotherapy). The median number of prior chemotherapy lines including adjuvant (range) was 2 (0–3). This study showed that compound II can be used to patients that have had prior chemotherapy lines that include the use of neurotoxic anticancer agents. In patients that have had prior chemotherapy lines that use neurotoxic anticancer agents, however, it is preferably, that the cumulative dose of compound II does not exceed about 200 mg/m² per cycle.

The study further showed that breast tumors and colon tumors, in patients previously treated with chemotherapy, responded to treatment with compound II. Specifically, breast cancer patients previously treated with adriamycin and taxotere with cyclophosphamide, 5-fluorouracil, methotrexate adjuvant therapy; adriamycin and taxotere with cyclophosphamide, 5-fluorouracil, methotrexate adjuvant therapy; or adriamycin, cyclophosphamide, 5-fluorouracil for metastatic cancer responded to treatment with compound II. Patients with metastatic colon cancer previously treated with taxol and carboplatin; 5-fluorouracil and leucovorin; or irinotecan responded to treatment with compound II.

Example 3
Pharmacokinetics of Compound II Orally Administered to Cancer Patients Patients with Advanced Malignancies were administered Compound II weekly as a 30-minute infusion (a course=3 intravenous weekly administrations). Patients received doses of 1, 2.5, 5, 10, 20, 25, or 30 mg/m². Starting at the 20 mg/m² dose level, a single oral dose of Compound II was given on day 6 in a vehicle of 80% propylene glycol and 20% ethanol (v/v) followed by administration of a citrate/phosphate buffer (22.5 gm) before course 1 to assess the absolute bioavailability of Compound II. The dose of oral Compound II administered on Day 6 matched the dose of IV Compound II administered on day 1. Serial plasma sampling was obtained on day 6 and day 1 of course 1 to assess pharmacokinetics by an LC/MS/MS.

Samples were analyzed by adding an internal standard to 0.2 mL of plasma sample, precipitating with acetone, and then extracting the supernatant with 1-chlorobutane. The organic layer was removed and evaporated to dryness. The residue was reconstituted and injected into the LC/MS/MS system. Chromatographic separation was achieved, isocratically, on a YMC ODS-AQ column (4.6×50 mm, 3:m) with a mobile phase of acetonitrile:0.01M ammonium acetate, pH 5.0 (65:35). Detection was by negative electrospray tandem mass spectrometry. The standard curve, which ranged from 2 to 500 ng/mL for all analytes and was fitted to a 1/x weighted quadratic regression model.

Compound II for oral administration, 25 mg/vial, was supplied as "drug in bottle." The vehicle (buffer) for constitution of Compound II, 25 mg/vial, was a mixture of 80% propylene glycol and 20% ethanol (v/v). The propylene glycol/ethanol mixture was prepared by mixing 80 parts by volume of propylene glycol and 20 parts by volume of ethanol in a suitable container and gently swirling the container until the solution was completely mixed.

The citrate/phosphate buffer for oral administration after compound II was supplied in a separate bottle. Buffer for use with Compound II was constituted with water for injection (WFI).

Compound II was prepared for administration to patients by using a suitable syringe to slowly inject 2.5, 5, or 10 mL of the propylene glycol/ethanol mixture into the 20 cc vial containing 25 mg/vial of Compound II, to give concentrations of 10, 5, or 2.5 mg/mL, respectively, depending on the dose to be administered to the patient. The syringe was removed and the vial shaken vigorously for 10 seconds. The vial was placed in a sonication bath and sonicated until the solution became clear. Vials were pooled depending on the dose.

The buffer for administration with Compound II was supplied in an 8 oz. clear glass bottle and was constituted with water for injection (WFI). The child resistant cap was removed from the bottle of buffer and about 140 mL of water for injection (WFI) were added. The bottle was shaken vigorously or sonicated with intermittent shaking until a clear solution was obtained.

Following oral administration on day 6, 7 mL blood samples was collected into Becton Dickinson Vacutainer tubes with K3EDTA as anticoagulent (lavender-colored top) according to the following schedule (expressed as hours:minutes from the start of the oral administration): predose, 00:15, 00:30, 00:45, 1:00, 1:30, 2:00, 3:00, 4:00, 6:00, 8:00, 24:00, 48:00, and 72:00. Following IV administration on day 1, 7 mL blood samples were collected into Becton Dickinson Vacutainer tubes with K3EDTA as anticoagulent (lavender-colored top) according to the following schedule (expressed as hours:minutes from the start of the IV infusion):predose, 00:15, 00:30 (end-of infusion), 00:45, 1:00, 1:30, 2:00, 3:00, 4:00, 6:00, 8:00, 24:00, 48:00, and 72:00.

Immediately after blood collection, the Vacutainer tubes were inverted several times to ensure mixing with the anticoagulant and then immediately placed on crushed ice. Within 30 minutes of collection, samples were centrifuged for 5 minutes at approximately 2000×g and 0 to 5 EC. The plasma was then transferred to separate pre-labeled screw-capped polypropylene tubes and stored at −70 EC until bioanalysis. Plasma concentrations of Compound II were analyzed using the LC/MS/MS assay.

The plasma concentration versus time data were analyzed using non-compartmental methods. The pharmacokinetic parameters determined for Compound II included the maximum observed plasma concentration (Cmax), time to reach Cmax (Tmax), area under the plasma concentration time curve from time zero to the time of last sampling time T(AUC(0-T)).

A total of 18 patients have received oral Compound II as a solution on day 6 and by IV on day 1. The summary of the pharmacokinetic results from these patients is presented in Table 1.

TABLE 1

Summary of Pharmacokinetics of Patients Administered Compound II Orally and Intravenously

| Dose (mg/m²) | 20 | | 25 | | 30 | |
| --- | --- | --- | --- | --- | --- | --- |
| N | 3 | | 11 | | 4 | |
| Route | IV | Oral | IV | Oral | IV | Oral |
| Formulation | IV | Solution for Oral Admin. | IV | Solution for Oral Admin. | IV | Solution for Oral Admin. |
| CMAX[a] (ng/mL) | 251 (108) | 142 (106) | 447 (189) | 180 (110) | 711 (530) | 274 (104) |
| TMAX[b] (h) | 0.25 (0.25, 0.25) | 1.0 (0.25, 1.50) | 0.50 (0.25, 0.50) | 0.50 (0.25, 3.00) | 0.50 (0.25, 0.50) | 0.50 (0.25, 0.75) |
| AUC(0-T)[a,c] (H · ng/mL) | 796 (587) | 404 (381) | 848 (284) | 533 (577) | 1155 (292) | 708 (291) |
| % F[a] | NA | 43.5 (16.1) | NA | 55.6 (18.4) | NA | 62.2 (25.1) |

[a]Mean (SD)
[b]Median (min, max)
[c]Represents AUC(0-T)

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A process for formulating, for parenteral administration, an epothilone analog represented by formula I:

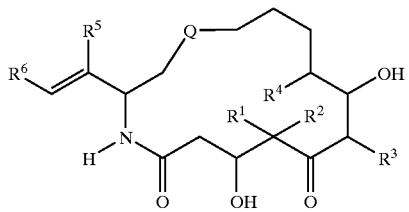

wherein:

Q is selected from the group consisting of:

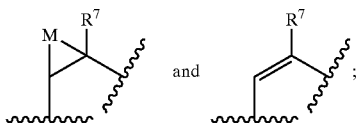

and

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein $R^1$, and $R^2$, are alkyl, they can be joined to form cycloalkyl;

$R^6$, is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{14}$, C=O, $R^{12}$OC=O and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}$C=O, and $R^{15}$OC=O;

and any salts, solvates, or hydrates thereof, comprising the following steps carried out under protection from light:

a) dissolving said epothilone analog in a mixture of at least about 50% by volume tertiary-butanol in water to form a solution;

b) performing primary drying of said solution at a temperature of from about –10° C. to about –40° C. under high vacuum of from about 50 millitorr to about 300 millitorr for from about 24 hours to about 96 hours to form a dried product;

c) performing secondary drying of the resultant dried product at a temperature of from about 10° C. to about 30° C. under high vacuum of from about 50 millitorr to about 300 millitorr for from 24 hours to about 96 hours to provide a lyophilized product; and d) packaging said lyophilized product in a first vial in combination with a second vial containing a sufficient quantity of an equal mixture by volume of a suitable nonionic surfactant and anhydrous ethanol to effect solution thereof.

2. The process of claim 1 wherein said epothilone analog is represented by formula II:

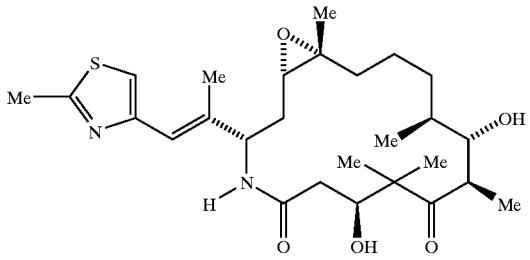

3. The process of claim 1 wherein in step a) said analog is first wetted with a mixture of at least about 60% tertiary-butanol in water, and then sufficient water, or a mixture of tertiary-butanol and water, is added thereto so that the resulting solution contains from about 2 mg/mL to about 30 mg/mL of said analog in a mixture of from about 50% to about 80% by volume tertiary-butanol in water.

4. The process of claim 2 wherein in step a) said analog is first wetted with a mixture of at least about 60% tertiary-butanol in water, and then sufficient water, or a mixture of tertiary-butanol and water, is added thereto so that the resulting solution contains from about 2 mg/mL to about 30 mg/mL of said analog in a mixture of from about 50% to about 80% by volume tertiary-butanol in water.

5. The process of claim 3 wherein in step a) said analog is initially wetted with a mixture of from about 60% to about 95% by volume tertiary-butanol in water.

6. The process of claim 4 wherein in step a) said analog is initially wetted with a mixture of from about 60% to about 95% by volume tertiary-butanol in water.

7. The process of claim 1 wherein said primary drying in step b) is carried out at a temperature of about –25° C. and a pressure of about 200 millitorr for about 48 hours.

8. The process of claim 2 wherein said primary drying in step b) is carried out at a temperature of about –25° C. and a pressure of about 200 millitorr for about 48 hours.

9. The process of claim 1 wherein said secondary drying in step c) is carried out at a temperature of about 25° C. and a pressure of about 150 millitorr for about 48 hours.

10. The process of claim 2 wherein said secondary drying in step c) is carried out at a temperature of about 25° C. and a pressure of about 150 millitorr for about 48 hours.

11. The process of claim 1 wherein said surfactant is polyethoxylated castor oil.

12. The process of claim 2 wherein said surfactant is polyethoxylated castor oil.

13. The process of claim 11 wherein said second vial contains an amount of said mixture sufficient to form a solution of from about 2 mg/mL to about 4 mg/mL of said analog therein.

14. The process of claim 12 wherein said second vial contains an amount of said mixture sufficient to form a solution of from about 2 mg/mL to about 4 mg/mL of said analog therein.

15. A pharmaceutical preparation comprising, a first vial containing a lyophilized epothilone analog and a second vial containing a quantity of a solvent for the lyophilized epothilone said solvent comprising a mixture of about equal parts by volume of dehydrated ethanol and a suitable nonionic surfactant, said analog being represented by formula I:

19

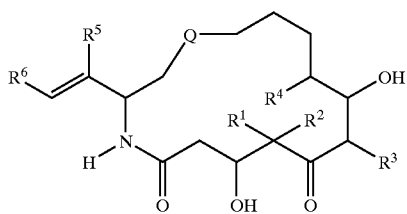

wherein:

Q is selected from the group consisting of

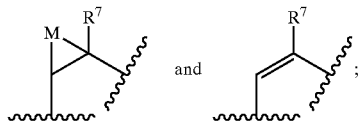

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein $R^1$ and $R^2$ are alkyl, they can be joined to form cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C{=}O$, $R^{12}OC{=}O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C{=}O$, and $R^{15}OC{=}O$;

and any salts, solvates, or hydrates thereof.

16. The pharmaceutical preparation of claim 15 wherein said epothilone analog is represented by formula II:

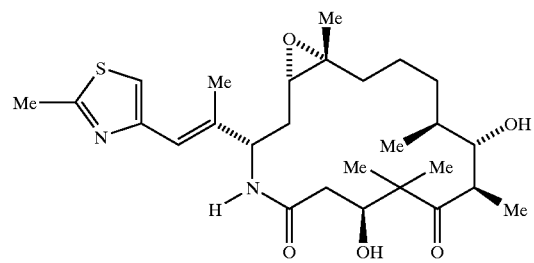

II.

17. The pharmaceutical preparation of claim 15 wherein said nonionic surfactant is polyethoxylated castor oil.

18. A process for forming a pharmaceutical composition for parenteral administration comprising mixing the contents of the vials of the pharmaceutical preparation of claim 15 to effect solution of said lyophilized epothilone analog and diluting the resultant solution with a quantity of a suitable parenteral diluent such that the concentration of said analog therein will be from about 0.1 mg/mL to about 0.9 mg/mL.

19. A process for forming a pharmaceutical composition for parenteral administration comprising mixing the contents of the vials of the pharmaceutical preparation of claim

20

16 to effect solution of said lyophilized epothilone analog and diluting the resultant solution with a quantity of a suitable parenteral diluent such that the concentration of said analog therein will be from about 0.1 mg/mL to about 0.9 mg/mL.

20. A process for forming a pharmaceutical composition for parenteral administration comprising mixing the contents of the vials of the pharmaceutical preparation of claim 17 to effect solution of said lyophilized epothilone analog and diluting the resultant solution with a quantity of a suitable parenteral diluent such that the concentration of said analog therein will be from about 0.1 mg/mL to about 0.9 mg/mL.

21. The process of claim 18 wherein said diluent is Lactated Ringer's Injection.

22. The process of claim 19 wherein said diluent is Lactated Ringer's Injection.

23. The process of claim 20 wherein said diluent is Lactated Ringer's Injection.

24. A method for treating a patient in need of treatment with an epothilone analog represented formula I:

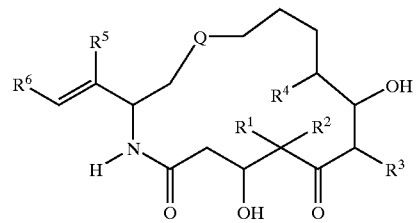

wherein:

Q is selected from the group consisting of M,

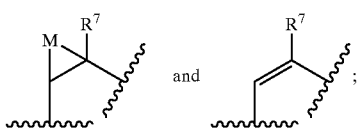

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C{=}O$, $R^{12}OC{=}O$ and $R^{13}SO_2$, and each $R^9$ and $R^{10}$ is, independently, selected from the group consisting of hydrogen, halogen, alkyl, substituted alkyl, aryl, heterocyclo, hydroxy, $R^{14}C{=}O$, and $R^{15}OC{=}O$;

and any salts, solvates, or hydrates thereof, comprising administering to said patient, by intravenous injection or infusion, an effective amount of a pharmaceutical composition of claim 18.

25. A method for treating a patient in need of treatment with an epothilone analog represented formula I:

21

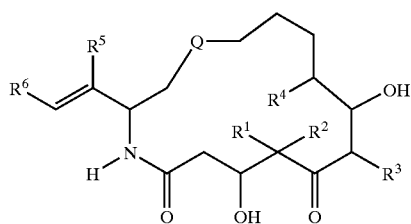

wherein:

Q is selected from the group consisting of

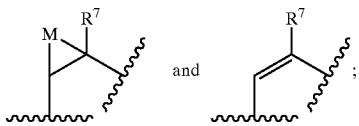

M is selected from the group consisting of oxygen, sulfur, $NR^8$ and $CR^9R^{10}$;

each $R^1$, $R^2$, $R^3$, $R^4$, $R^5$, $R^7$, $R^{11}$, $R^{13}$, $R^{14}$, and $R^{15}$ is, independently, selected from the group consisting of hydrogen, alkyl, substituted alkyl, aryl, substituted aryl and heterocyclo, and wherein R' and $R^2$ are alkyl, they can be joined to form a cycloalkyl; and $R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}$, C=O, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any salts, solvates, or hydrates thereof, comprising administering to said patient, by intravenous injection or infusion, an effective amount of a pharmaceutical composition of claim 19.

26. A method for treating a patient in need of treatment with an epothilone analog represented formula I:

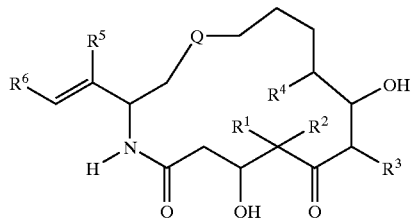

wherein:

Q is selected from the group consisting of

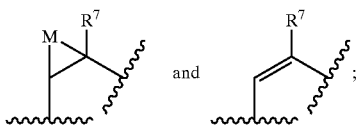

M is selected from the group consisting of oxygen, sulfur, $NR^8$ and $CR^9R^{10}$;

22 each R', $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo; $R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any salts, solvates, or hydrates thereof, comprising administering to said patient, by intravenous injection or infusion, an effective amount of a pharmaceutical composition of claim 20.

27. The method of claim 24 wherein said diluent is Lactated Ringer's Injection.

28. The method of claim 25 wherein said diluent is Lactated Ringer's Injection.

29. The method of claim 26 wherein said diluent is Lactated Ringer's Injection.

30. A pharmaceutical composition suitable for parenteral administration comprising in lyophilized form a compound represented by formula I:

I

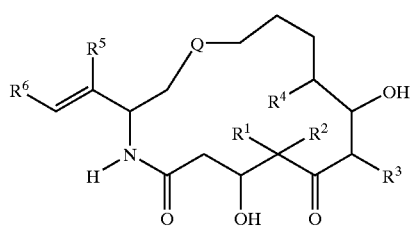

wherein:

Q is selected from the group consisting of

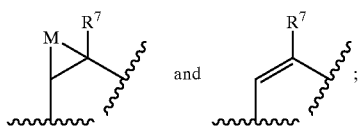

M is selected from the group consisting of oxygen, sulfur, $NR^8$, and $CR^9R^{10}$;

each R', $R^2$, $R^3$, $R^4$, $R^5$, $R^7$, $R^{11}$, $R^{12}$, $R^{13}$, $R^{14}$ and $R^{15}$ independently, selected from the group consisting of hydrogen, alkyl, substituted alkyl, aryl, substituted aryl and heterocyclo, and wherein R' and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^2OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any salts, solvates, or hydrates thereof;
dehydrated alcohol;
and a non-ionic surfactant.

31. The composition of claim 30, wherein the surfactant is polyethoxylated castor oil.

32. The composition of claim 30, wherein the surfactant is Cremophor EL®.

33. The composition of claim 30, wherein the concentration of the compound of formula I is from about 2 mg/mL to 4 mg/mL.

34. A pharmaceutical composition suitable for parenteral administration comprising a compound represented by formula II:

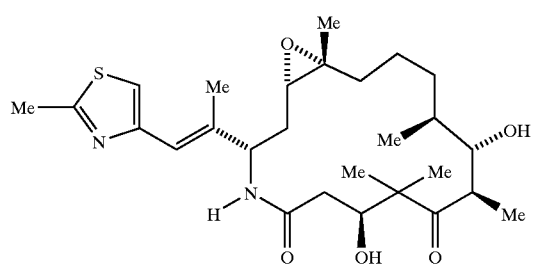

II and any salts, solvates, or hydrates thereof:
dehydrated alcohol; and
a non-ionic surfactant.

35. A method of treating cancer in a patient comprising intravenously administering to said patient a therapeutically effective amount of the pharmaceutical formulation of claim 30 diluted in a parenteral diluent.

36. The method of claim 35, wherein the parenteral diluent is 5% dextrose, lactated ringer's and dextrose injection, or sterile water for injection.

37. The method of claim 35, wherein the concentration of the compound of formula I in the parenteral diluent is about 0.1 mg/mL to 0.9 mg/mL.

38. The method of claim 35, wherein the compound of formula I is administered in a dose of about 1 mg/m$^2$ to 65 mg/m$^2$.

39. The method of claim 35, wherein the compound of formula I is administered at a dose of about 25 mg/m$^2$.

40. The method of claim 35, wherein the pharmaceutical composition is administered weekly as an IV infusion.

41. The method of claim 35, wherein the IV infusion is administered over a period of about 45 minutes to 90 minutes.

42. The method of claim 35, wherein the IV infusion is administered over a period of about 1 hour.

43. The method of claim 35, further comprising administering to said patient one or more additional agents to prevent nausea, vomiting, hypersensitivity, or gastric irritation.

44. The method of claim 43, wherein the one or more additional agents is an H1 or H2 antihistamine.

45. The method of claim 35, wherein the patient has not previously been treated for cancer.

46. The method of claim 35, wherein the patient has been previously treated for cancer.

47. The method of claim 35, wherein the cancer is refractory to radiation therapy.

48. The method of claim 35, wherein the cancer is refractory to anti-cancer chemotherapy.

49. A method of treating cancer in a patient previously experiencing neurotoxicity comprising intravenously administering to said patient a therapeutically effective amount of the pharmaceutical formulation of claim 30 diluted in a parenteral diluent as a weekly infusion, wherein the total dose of the compound of formula I is less than about 200 mg/m$^2$.

50. The method of claim 35, wherein the cancer is a solid tumor.

51. The method of claim 29, wherein the cancer is a solid tumor.

52. A method of treating cancer while reducing or avoiding neurotoxicity which comprises intravenously administering a therapeutically effective amount of compound represented by formula I:

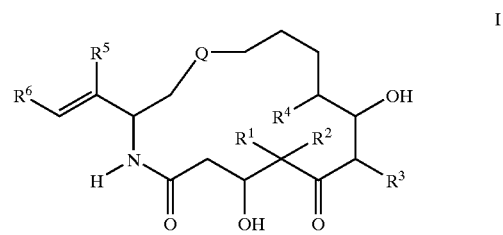

I wherein:

Q is selected from the group consisting of

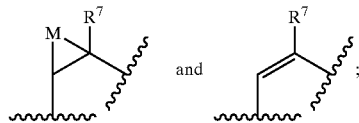

M is selected from the group consisting of oxygen, sulfur, NR$^8$ and CR$^9$, R$^{10}$, each R$^1$, R$^2$, R$^3$, R$^4$, R$^5$, R$^7$, R$^{11}$, R$^{12}$, R$^{13}$, R$^{14}$ and R$^{15}$ is, independently, selected from the group consisting of hydrogen, alkyl, substituted alkyl, aryl, substituted aryl and heterocyclo, and wherein R' and R$^2$ are alkyl, they can be joined to form a cycloalkyl;

R$^6$ is selected from the group consisting of hydrogen, alkyl, substituted alkyl, aryl, substituted aryl, cycloalkyl, heterocyclo and substituted heterocyclo;

R$^8$ is selected from the group consisting of hydrogen, alkyl, substituted alkyl, R$^{11}$C=O, R$^{12}$OC=O and R$^{12}$SO$_2$ and each R$^9$ and R$^{10}$ is, independently, selected from the group consisting of hydrogen, halogen, alkyl, substituted alkyl, aryl, heterocyclo, hydroxy, R$^{14}$C=O, and R$^{15}$OC=O;

and any salts, solvates, or hydrates thereof;
over a period of one (1) hour to a patient in need thereof.

53. The method of claim 52, wherein the infusion is made on a weekly basis.

54. The method of claim 52, wherein the therapeutically effective amount is from about 1 mg/m$^2$ to about 65 mg/m$^2$.

55. The method of claim 54, wherein the amount is 25 mg/m$^2$.

56. A method of treating cancer while reducing or avoiding neurotoxicity which comprises intravenously infusing a therapeutically effective amount of compound represented by formula I:

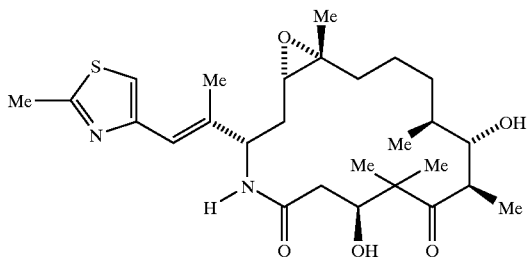

over a period of one (1) hour to a patient in need thereof.

57. The method of claim 56 which further comprises orally administering said compound 1 week before or after an intravenous administration.

58. A method of treating cancer in a human patient in need thereof with a synthetic or semi-synthetic epothilone analogue that is active against cancer which comprises a four (4) week dosing cycle wherein said cycle comprises three weeks of weekly intravenous administration and one week of oral administration of said epothilone analogue.

59. The method of claim 58 wherein the compound is administered daily for 3 days with a period of 1 week to 3 weeks between cycles where there is no administration of the compound.

60. The method of claim 58 wherein the compound is administered daily for 3 days with a period of 1 week to 3 weeks between cycles where there is no administration of the compound.

61. The method of claim 58 wherein the compound is administered daily for 5 days with a period of 1 week to 3 weeks between cycles where there is no administration of the compound.

62. The method of claim 58 wherein the compound is administered daily for 5 days with a period of 1 week to 3 weeks between cycles where there is no administration of the compound.

63. A method of treating cancer in a patient comprising orally administering to said patient daily for 3 days, daily for 5 days, or weekly a therapeutically effective amount of a compound represented by formula I:

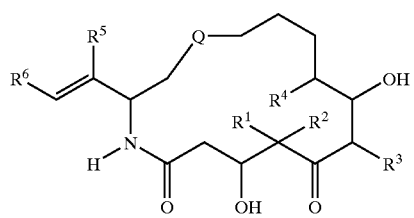

wherein:
Q is selected from the group consisting of

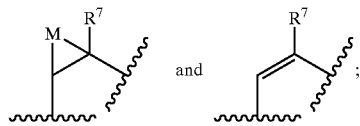

M is selected from the group consisting of oxygen, sulfur, $NR^8$ and $CR^9R^{10}$;

each $R^1$, $R^2$, $R^3$, $R^4$, $R^5$, $R^7$ $R^{11}$ $R^{12}$ $R^{13}$ $R^{14}$ and $R^{15}$ is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C{=}O$, $R^{12}OC{=}O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C{=}O$, and $R^{15}OC{=}O$;

and any salts, solvates, or hydrates thereof.

64. The method of claim 63, wherein the compound of formula I is administered in a dose of about 0.05 mg/kg to 200 mg/kg.

65. The method of claim 64, wherein the compound of formula I is administered at a dose of about 1 mg/m² to 65 mg/m².

66. The method of claim 64, wherein the compound is administered every 3 weeks.

67. The method of claim 63 wherein the compound is administered daily for 3 days with a period of 1 week to 3 weeks between cycles where there is no administration of the compound.

68. The method of clam 66 wherein the compound is administered daily for 5 days with a period of 1 week to 3 weeks between cycles where there is no administration of the compound.

69. The method of claim 66 wherein the compound is administered daily for 3 days with a period of 4 days between cycles where there is no treatment.

70. The method of claim 66 wherein the compound is administered daily for 5 days with a period of 2 days between cycles where there is no treatment.

71. The pharmaceutical preparation of claim 1, wherein the lyophilized epothilone analog is free of excipients.

72. The pharmaceutical preparation of claim 15, wherein the lyophilized epothilone analog is free of excipients.

73. The pharmaceutical preparation of claim 16, wherein the lyophilized epothilone analog is free of excipients.

74. A process for forming a pharmaceutical composition for parenteral administration comprising mixing the contents of the vials of the pharmaceutical preparation of claim 72 to effect solution of said lyophilized epothilone analog and diluting the resultant solution with a quantity of a suitable parenteral diluent such that the concentration of said analog therein will be from about 0.1 mg/mL to about 0.9 mg/mL.

75. A process for forming a pharmaceutical composition for parenteral administration comprising mixing the contents of the vials of the pharmaceutical preparation of claim 73 to effect solution of said lyophilized epothilone analog and diluting the resultant solution with a quantity of a suitable parenteral diluent such that the concentration of said analog therein will be from about 0.1 mg/mL to about 0.9 mg/mL.

76. A method of treating cancer in a patient comprising intravenously and orally administering to said patient a therapeutically effective amount of a compound represented by formula II:

II.

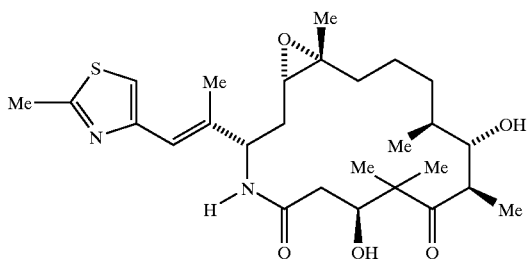

77. A method of treating cancer in a patient comprising intravenously administering to said patient a therapeutically effective amount of the compound of claim 76 diluted in a parenteral diluent.

78. The pharmaceutical preparation of claim 15, wherein the quantity of solvent is an amount such that when the solvent is combined with the lyophilized epothilone the resulting solution contains from about 2 mg/mL to about 4 mg/mL of said analog.

79. A method of treating cancer in a patient comprising intravenously administering to said patient daily for 3 days or daily for 5 days a therapeutically effective amount of a compound represented by formula I:

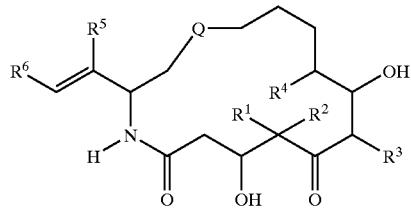

wherein:

Q is selected from the group consisting of

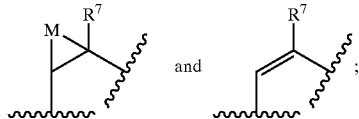

M is selected from the group consisting of oxygen, sulfur, NR, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$, is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any salts, solvates, or hydrates thereof.

80. The method of claim 79, wherein the compound of formula I is administered daily for 3 days.

81. The method of claim 79, wherein the compound of formula I is administered daily for 5 days.

82. The method of claim 81, wherein the compound of formula I is administered in a dose of about 0.05 mg/kg to 200 mg/kg.

83. The method of claim 79, wherein the compound of formula I is administered at a dose of about 1 mg/m$^2$ to 65 mg/m$^2$.

84. The method of claim 83, wherein the compound of formula I is administered at a dose of about 25 mg/m$^2$.

85. The method of claim 79, wherein the IV infusion is administered over a period of about 45 minutes to 90 minutes.

86. The method of claim 79, wherein the IV infusion is administered over a perioe of about 1 hour.

87. The method of claim 79, further comprising administering to said patient one or more additional therapeutic agents to prevent nausea, vomiting, hypersensitivity, or gastric irritation.

88. The method of claim 86, wherein the one or more additional therapeutic agents is an $H^1$, or $H^2$, antihistamine.

89. The method of claim 79, wherein the patient has not previously been treated for cancer.

90. The method of claim 86, wherein the patient has been previously treated for cancer.

91. The method of claim 79, wherein the cancer is refractory to radiation therapy.

92. The method of 79, wherein the cancer is refractory to anti-cancer chemotherapy.

93. A method of treating cancer in a patient comprising intravenously administering to said patient every week or every 3 weeks a therapeutically effective amount of a compound represented by formula I:

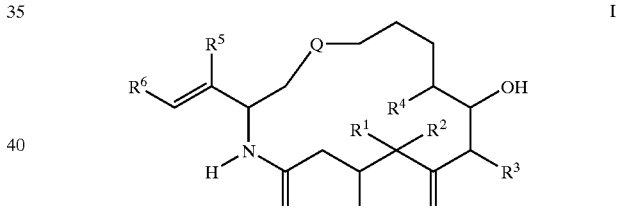

wherein:

Q is selected from the group consisting of

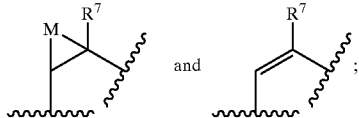

M is selected from the group consisting of oxygen, sulfur, NR, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$, is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any salts, solvates, or hydrates thereof.

94. The method of 93, wherein the compound of formula I is administered every week.

95. The method of 93, wherein the compound of formula I is administered every 3 weeks.

96. The method of claim 95, further comprising orally administering the compound of formula I before the 3 week cycle.

97. The method of claim 95, further comprising orally administering the compound of formula I after the 3 week cycle.

98. The method of claim 97, wherein the compound of formula I is administered as one or more 28 day cycles, wherein the compound of formula I is administered as an IV infusion on days 1, 7, and 14 and orally on day 21.

99. The method of claim 93, wherein the IV infusion is administered over a period of about 1 hour.

100. The method of claim 93, further comprising administering to said patient one or more additional therapeutic agents to prevent nausea, vomiting, hypersensitivity, or gastric irritation.

101. The method of claim 100, wherein the one or more additional therapeutic agents is an $H^1$, or $H^2$, antihistamine.

102. The method of claim 93, wherein the patient has not previously been treated for cancer.

103. The method of claim 93, wherein the patient has been previously treated for cancer.

104. The method of claim 93, wherein the cancer is refractory to radiation therapy.

105. The method of claim 93, wherein the cancer is refractory to anti-cancer chemotherapy.

* * * * *

Disclaimer

6,670,384 B2 — Rebanta Bandyopadhyay, Portage, MI (US); Timothy M. Malloy, Yardley, PA (US); Andrea Panaggio, West Windsor, NJ (US); Krishnaswamy Srinivas Raghavan, Cranbury, NJ (US); Sailesh Amilal Varia, Princeton Junction, NJ (US). Patent dated Dec. 30, 2003. Disclaimer filed May 16, 2005, by the assignee, Bristol-Myers Squibb Company.

The term of this patent shall not extend beyond the expiration date of Patent No. 6,576,651.
*(Official Gazette, April 22, 2008)*

(12) EX PARTE REEXAMINATION CERTIFICATE (5663rd)
United States Patent
Bandyopadhyay et al.

(10) Number: US 6,670,384 C1
(45) Certificate Issued: *Jan. 23, 2007

(54) METHODS OF ADMINISTERING EPOTHILONE ANALOGS FOR THE TREATMENT OF CANCER

(75) Inventors: Rebanta Bandyopadhyay, Portage, MI (US); Timothy M. Malloy, Yardley, PA (US); Andrea Panaggio, West Windsor, NJ (US); Krishnaswamy Srinivas Raghavan, Cranbury, NJ (US); Sailesh Amilal Varia, Princeton Junction, NJ (US)

(73) Assignee: Bristol-Myers Squibb Company, Princeton, NJ (US)

Reexamination Request:
No. 90/007,605, Jun. 27, 2005

Reexamination Certificate for:
Patent No.: 6,670,384
Issued: Dec. 30, 2003
Appl. No.: 10/055,653
Filed: Jan. 23, 2002

( * ) Notice: This patent is subject to a terminal disclaimer.

Related U.S. Application Data

(60) Provisional application No. 60/264,228, filed on Jan. 25, 2001, and provisional application No. 60/290,008, filed on May 11, 2001.

(51) Int. Cl.
*A61K 31/365* (2006.01)

(52) U.S. Cl. ............................ 514/365; 514/183
(58) Field of Classification Search ............ None
See application file for complete search history.

(56) References Cited

U.S. PATENT DOCUMENTS

| | | | |
|---|---|---|---|
| 4,950,432 A | 8/1990 | Mehta et al. | 264/4.6 |
| 6,380,395 B1 | 4/2002 | Vite et al. | 548/146 |

*Primary Examiner*—Phyllis G. Spivack

(57) ABSTRACT

A process for formulating certain epothilone analogs for parenteral administration is disclosed wherein the analog is dissolved in a mixture of at least 50% by volume tertiary-butanol in water, the mixture is lyophilized, the resulting lyophilized product is packaged in one vial with a sufficient amount of solvent comprising anhydrous ethanol and a suitable nonionic surfactant in a second vial. All steps are carried out with protection from light. In use, the contents of the second or diluent vial are added to the lyophilized product and mixed to constitute the epothilone analog and the resulting solution is diluted with a suitable diluent to produce a solution for intravenous injection containing the epothilone analog in a concentration of from about 0.1 mg/mL to about 0.9 mg/mL. A preferred surfactant is polyethoxylated castor oil and a preferred diluent is Lactated Ringer's Injection.

ID1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, line 66 to column 3, line 4:

As discussed herein a wide variety of cancers are encompassed by the methods of the present invention. In a preferred embodiment, the methods of the invention are for the treatment of solid tumors including but not limited to breast, head and neck, sarcoma, colorectal, UPT, melanoma, [oesophagus] *esophagus*, renal, cervix, thyroid, anal, ovarian, and colon.

Column 3, lines 57–61:

each $R^1$, $R^2$, $R^3$, $R^4$, $R^5$, $R^7$, $R^{11}$, $R^{12}$, $R^{13}$ [and] $R^{14}$ *and $R^{15}$* is, independently, selected from the group consisting of hydrogen, alkyl, substituted alkyl, aryl, substituted aryl and heterocyclo, and wherein $R^1$ and $R^2$ are alkyl, they can be joined to form cycloalkyl;

Column 4, lines 16–41:

The term "substituted alkyl" refers to an alkyl group substituted by, for example, one to four substituents, such as, halo, trifluoromethyl, trifluoromethoxy, hydroxy, alkoxy, [cycloalkyoxy] *cycloalkoxy*, [heterocylooxy] *heterocyclyloxy*, oxo, alkanoyl, aryl, aryloxy, aralkyl, alkanoyloxy, amino, alkylamino, arylamino, aralkylamino, cycloalkylamino, [heterocycloamino] *heterocyclylamino*, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, [heterocyclothio] *heterocyclylthio*, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and [heterocyclos] *heterocycles*, such as, indolyl, imidazolyl, furyl, thienyl, thiazolyl, [pyrrolidyl] *pyrrolidinyl*, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

Column 4, line 58 to column 5, line 14:

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, [heterocylooxy] *heterocycyloxy*, alkanoyl, alkanoyloxy, amino, alkylamino, dialkylamino, aralkylamino, cycloalkylamino, [heterocycloamino] *heterocyclylamino*, alkanoylamino, thiol, alkylthio, cycloalkylthio, [heterocyclothio] *heterocyclylthio*, ureido, nitro, cyano, carboxy, carboxyalkyl, carbamyl, alkoxycarbonyl, alkylthiono, arylthiono, alkylsulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

Column 5, lines 27–40:

Exemplary monocyclic heterocyclic groups include pyrrolidinyl, pyrrolyl, [indolyl,] pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, [and] triazolyl, *and the like*.

Column 5, lines 41–57:

Exemplary bicyclic heterocyclic groups include *indolyl*, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, [furo[3,1-b]pyridinyl]] *furo[3,1-b]pyridinyl* or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Column 6, lines 51–55:

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and [Burketts] *Burkitts* lymphoma;

Column 6, lines 59–60:

[tumors of mesenchymal origin, including fibrosarcoma and rhabdomyosarcoma;]

Column 6, lines 66–67:

tumors of mesenchymal origin, including fibrosarcoma, [rhabdomyoscaroma] *rhabdomyosarcoma*, and osteosarcoma; and Column 7, lines 33–44:

Each of the compounds represented by formulae I and II may also be formulated or co-administered with other therapeutic agents that are selected for their particular usefulness in administering therapies [associates] *associated* with the aforementioned conditions. For example, each of the compounds of formulae I and II may be formulated with agents to prevent nausea, hypersensitivity, and gastric irritation, such as anti-emetics, and $H_1$ and $H_2$ antihistamines. The Column 7, line 45 to column 8, line 10:

Furthermore, compounds of formulae I or II may be administered in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g., S phase, than the present compounds of formula I and II which exert their effects at the $G_2$-M phase. Example classes of anti-cancer and cytotoxic agents include, but are not limited to, alkylating agents, such as [nitorgen] *nitrogen* mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®); plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. Compounds represented by formulae I and II may also be used in conjunction with radiation therapy.

Column 8, lines 11–27:

Representative examples of these classes of anti-cancer and cytotoxic agents include, but are not limited to, mechlorethamine [hydrochlordie] *hydrochloride*, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Column 9, lines 33–43:

It has unexpectedly been found that the stability of the subject epothilone analogs can be significantly enhanced by carrying out the preparation of the solution at a temperature below ambient, preferably from about [5EC] *5° C.* to about [15EC] *15° C.*, more preferably about [5EC] *5° C.* Further, both the process of forming the solution and subsequent lyophilization are to be carried out in vessels such that the epothilone analogs are protected from exposure to light. It is also beneficial to carry out the lyophilization in comparatively small batches so that the epothilone analogs are exposed to an aqueous medium for a minimum amount of time.

Column 9, lines 44–55:

The primary drying stage of lyophilization of the solution formed as described above is carried out at temperatures from about [−10EC to about −40EC] *−40° C. to about −10° C.*, preferably about [−25 EC] *−25° C.*, under high vacuum, ie., from about 50 millitorr to about 300 millitorr, preferably about 200 millitorr, for an extended period, i.e., from about 24 hours to about 96 hours, preferably about 48 hours. Lyophilization in this temperature range produces an amorphous product which is desirable for an intravenous preparation. Those of ordinary skill in the art will appreciate that conventional procedures, such as powder X-ray diffraction, can be utilized to confirm the amorphous nature of the lyophilized product.

Column 9, lines 56–62:

The residual solvents in the product are removed by a secondary drying stage that is carried out at comparatively low temperatures, i.e., from about [10 EC] *10° C.* to about [30 EC] *30° C.*, preferably about [25 EC] *25° C.*, under high vacuum, i.e., from about 50 millitorr to about 300 millitorr, preferably about 150 millitorr for an extended period, i.e., from about 24 hours to about 96 hours, preferably about 48 hours.

Column 10, lines 28–38:

The final dilution of the reconstituted epothilone analog in the formulation of the invention may be carried out with other preparations having similar utility, for example, 5% Dextrose Injection, Lactated Ringer's and Dextrose Injection, Sterile Water for Injection, and the like. However, because of its narrow pH range, pH 6.0 to 7.5, Lactated Ringer's Injection is preferred. Per 100 mL, Lactated Ringer's Injection contains Sodium Chloride USP 0.6 g, Sodium Lactate 0.31 g, Potassium chloride USP 0.03 g and [Calcium Chloride-2H20] *Calcium Chloride·2H$_2$O* USP 0.02 g. The osmolarity is 275 mOsmol/L, which is very close to isotonicity.

Column 11, lines 40–43:

One of ordinary skill in the art would readily know how to convert doses from mg/kg to [mg/m2] *mg/m$^2$* given either or both the height and or weight of the patient (See, e.g., http://www.fda.gov/cder/cancer/animalframe.htm).

Column 13, line 66 to column 14, line 11:

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, 9.86 g, was wetted/partially dissolved with 600 mL of a 9:1 mixture of tertiary butanol and Water for Injection USP which had been pre-cooled to [5 EC] *5° C.* Once the drug powder had become completely wetted, dissolution was completed by the addition of 600 mL of a 1:9 mixture of tertiary butanol and Water for Injection and 766 mL of a 1:1 mixture of tertiary butanol and Water for Injection which likewise had been pre-cooled to [5 EC] *5° C.* thereby making the final solution a 1:1 mixture. The dissolution was carried out under protection from light.

Column 14, lines 12–20:

The solution formed above was promptly lyophilized in a Virtis INOTOP lyophilizer at [−16 EC] *−16° C.* under light [protectant] *protected* conditions over a period of 48 hours. The resultant lyophilized product (lyophile) was then further dried at [15 EC] *15° C.* under high vacuum for 48 hours. No detectable degradation of the drug was observed during these procedures. The lyophile was packaged under sterile conditions into 30 mL vials, each containing 10 mg of drug and standard excess to allow for vial/needle/syringe loss.

Column 14, lines 31–45:

A total of 24 cancer patients (12 male and 12 female) received compound II by IV administration to evaluate the maximum tolerated dose (MTD), the dose limiting toxicity (DLT), the [pharmacokinitics] *pharmacokinetics* and pharmacodynamics, and to evaluate the anti-tumor activity of compound II. The median age (range) of the patients was 57 (34–74). 5 patients had breast cancer, 5 patients had head and neck cancer, 2 patients had sarcoma, 2 patients had colorectal cancer, 2 patients had UPT cancer, 2 patients had melanoma, 2 patients had cancer of the esophagus, 1 patient had renal cancer, 1 patient had cervical cancer, 1 patient had thyroid cancer, and 1 patient had anal cancer. 21 patients had received prior chemotherapy (18 patients received neurotoxic agents and 18 patients received radiotherapy). The median number of prior chemotherapy lines including adjuvant (range) was 2 (1–3).

Column 15, lines 34–45:

Samples were analyzed by adding an internal standard to 0.2 mL of plasma sample, precipitating with acetone, and then extracting the supernatant with 1-chlorobutane. The organic layer was removed and evaporated to dryness. The residue was reconstituted and injected into the LC/MS/MS system. Chromatographic separation was achieved, isocratically, on a YMC ODS-AQ column (4.6×50 mm, 3:m) with a mobile phase of acetonitrile:0.01M ammonium acetate, pH 5.0 (65:35). Detection was by negative electrospray tandem mass spectrometry. The standard curve, which ranged from 2 to 500 ng/mL for all analytes[and], was fitted to a 1/x weighted quadratic regression model.

Column 16, lines 22–30:

Immediately after blood collection, the Vacutainer tubes were inverted several times to ensure mixing with the anticoagulant and then immediately placed on crushed ice. Within 30 minutes of collection, samples were centrifuged for 5 minutes at approximately 2000×g and 0 to [5 EC] *5° C*. The plasma was then transferred to separate pre-labeled screw-capped polypropylene tubes and stored at [–70 EC] *–70° C*. until bioanalysis. Plasma concentrations on Compound II were analyzed using the LC/MS/MS assay.

AS A RESULT OF REEXAMINATION, IT HAS BEEN DETERMINED THAT:

The patentability of claims 15–23, 63–70 and 72–77 is confirmed.

Claims 60, 62 and 71 are cancelled.

Claims 1, 7–10, 24–26, 30, 32, 34, 35, 44, 49, 52, 56, 58, 78, 79, 82, 86, 88, 93–95 and 101 are determined to be patentable as amended.

Claims 2–6, 11–14, 27–29, 31, 33, 36–43, 45–48, 50, 51, 53–55, 57, 59, 61, 80, 81, 83–85, 87, 89–92, 96–100 and 102–105, dependent on an amended claim, are determined to be patentable.

New claims 106–110 are added and determined to be patentable.

1. A process for formulating, for parenteral administration, an epothilone analog represented by formula I:

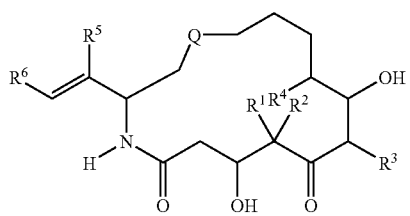

wherein:

Q is selected from the group consisting of:

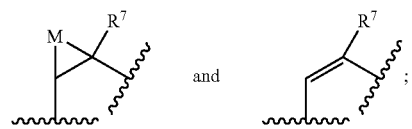

and

M is selected from the group consisting of oxygen, sulfur, $NR^8$, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein [$R^1$, and $R^2$,] $R^1$ and $R^2$ are alkyl, they can be joined to form cycloalkyl;

$R^6$[.] is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, [$R^{14}$, C=O] $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any [salts,] solvates, or hydrates thereof, comprising the following steps carried out under protection from light:

a) dissolving said epothilone analog in a mixture of at least about 50% by volume tertiary-butanol in water to form a solution;

b) performing primary drying of said solution at a temperature of from about [–10° C. to about –40° C.] *–40° C. to about –10° C.* under high vacuum of from about 50 millitorr to about 300 millitorr for from about 24 hours to about 96 hours to form a dried product;

c) performing secondary drying of the resultant dried product at a temperature of from about [10° C.] *10° C.* to about [30° C.] *30° C.* under high vacuum of from about 50 millitorr to about 300 millitorr for from 24 hours to about 96 hours to provide a lyophilized product; and d) packaging said lyophilized product in a first vial in combination with a second vial containing a sufficient quantity of an equal mixture by volume of a suitable nonionic surfactant and anhydrous ethanol to effect solution thereof.

7. The process of claim 1 wherein said primary drying in step b) is carried out at a temperature of about [−25° C.] −25° C. and a pressure of about 200 millitorr for about 48 hours.

8. The process of claim 2 wherein said primary drying in step b) is carried out at a temperature of about [−25° C.] −25° C. and a pressure of about 200 millitorr for about 48 hours.

9. The process of claim 1 wherein said secondary drying in step c) is carried out at a temperature of about [25° C.] 25° C. and a pressure of about 150 millitorr for about 48 hours.

10. The process of claim 2 wherein said secondary drying in step c) is carried out at a temperature of about [25° C.] 25° C. and a pressure of about 150 millitorr for about 48 hours.

24. A method for treating a patient in need of treatment with an epothilone analog represented *by* formula I:

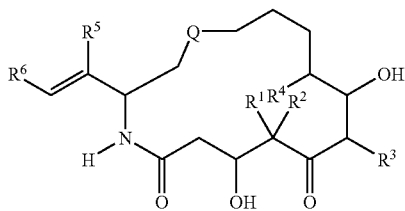

wherein:

Q is selected from the group consisting of [M,]

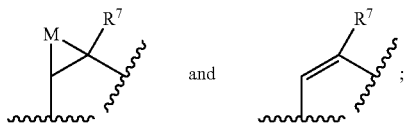

M is selected from the group consisting of oxygen, sulfur, NR$^8$, and CR$^9$R$^{10}$;

each R$^1$, R$^2$, R$^3$, R$^4$, R$^5$, R$^7$, R$^{11}$, R$^{12}$, R$^{13}$, R$^{14}$, and R$^{15}$ is, independently, selected from the group consisting of hydrogen, alkyl, substituted alkyl, aryl, substituted aryl and heterocyclo, and wherein R$^1$ and R$^2$ are alkyl, they can be joined to form a cycloalkyl;

R$^6$ is selected from the group consisting of hydrogen, alkyl, substituted alkyl, aryl, substituted aryl, cycloalkyl, heterocyclo and substituted heterocyclo;

R$^8$ is selected from the group consisting of hydrogen, alkyl, substituted alkyl, R$^{11}$C=O, R$^{12}$OC=O and R$^{13}$SO$_2$; and each R$^9$ and R$^{10}$ is, independently, selected from the group consisting of hydrogen, halogen, alkyl, substituted alkyl, aryl, heterocyclo, hydroxy, R$^{14}$C=O, and R$^{15}$OC=O;

and any [salts,] solvates, or hydrates thereof, comprising administering to said patient, by intravenous injection or infusion, an effective amount of a pharmaceutical composition *prepared according to the method* of claim 18.

25. A method for treating a patient in need of treatment with an epothilone analog represented formula I:

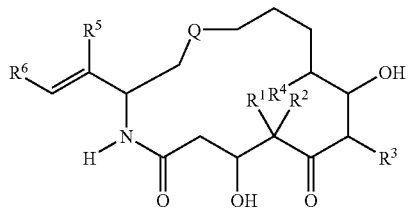

wherein:

Q is selected from the group consisting of

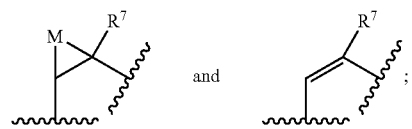

M is selected from the group consisting of oxygen, sulfur, NR$^8$, and CR$^9$R$^{10}$;

each R$^1$, R$^2$, R$^3$, R$^4$, R$^5$, R$^7$, R$^{11}$, *R$^{12}$*, R$^{13}$, R$^{14}$, and R$^{15}$ is independently, selected from the group consisting of hydrogen, alkyl, substituted alkyl, aryl, substituted aryl and heterocyclo, and wherein [R'] *R$^1$* and R$^2$ are alkyl, they can be joined to form a cycloalkyl; and R$^6$ is selected from the group consisting of hydrogen, alkyl, substituted alkyl, aryl, substituted aryl, cycloalkyl, heterocyclo and substituted heterocyclo;

R$^8$ is selected from the group consisting of hydrogen, alkyl, substituted alkyl, [R$^{11}$, C=O] *R$^{11}$C=O*, R$^{12}$OC=O and R$^{13}$SO$_2$; and each R$^9$ and R$^{10}$ is, independently, selected from the group consisting of hydrogen, halogen, alkyl, substituted alkyl, aryl, heterocyclo, hydroxy, R$^{14}$C=O, and R$^{15}$OC=O;

and any [salts,] solvates, or hydrates thereof, comprising administering to said patient, by intravenous injection or infusion, an effective amount of a pharmaceutical composition *prepared according to the method* of claim 19.

26. A method for treating a patient in need of treatment with an epothilone analog represented formula I:

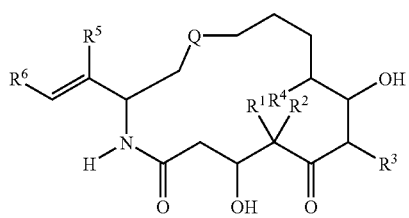

wherein:

Q is selected from the group consisting of

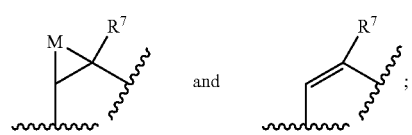

M is selected from the group consisting of oxygen, sulfur, NR$^8$, and CR$^9$R$^{10}$;

each [R'] $R^1$, $R^2$, $R^3$, $R^4$, $R^5$, $R^7$, $R^{11}$, $R^{12}$, $R^{13}$, $R^{14}$, and $R^{15}$ is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, [$R^{14C=O}$;] $R^{14}C=O$, and $R^{15}OC=O$;

and any [salts,] solvates, or hydrates thereof, comprising administering to said patient, by intravenous injection or infusion, an effective amount of a pharmaceutical composition *prepared according to the method* of claim 20.

30. A pharmaceutical composition suitable for parenteral administration comprising in lyophilized form a compound represented by formula I:

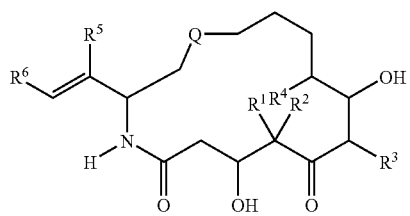

I wherein:

Q is selected from the group consisting of

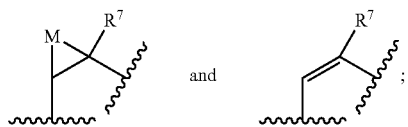

M is selected from the group consisting of oxygen, sulfur, $NR^8$, and $CR^9R^{10}$;

each [R'] $R^1$, $R^2$, $R^3$, $R^4$, $R^5$, $R^7$, $R^{11}$, $R^{12}$, $R^{13}$, $R^{14}$ and $R^{15}$ *is*, independently, selected from the group consisting of hydrogen, alkyl, substituted alkyl, aryl, substituted aryl and heterocyclo, and wherein [R'] $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, [$R^2OC=O$] $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}CO=O$, and $R^{15}OC=O$;

and any [salts,] solvates, or hydrates thereof; dehydrated alcohol;
and a [non-ionic] *nonionic* surfactant.

32. The composition of claim 30, wherein the surfactant is Cremophor EL® *surfactant*.

34. A pharmaceutical composition suitable for parenteral administration comprising a compound represented by formula II:

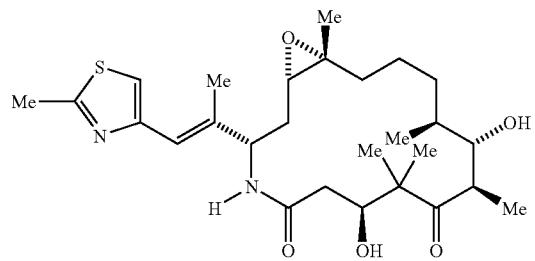

II and any [salts,] solvates, or hydrates thereof;
dehydrated alcohol; and
a [non-ionic] *nonionic* surfactant.

35. A method of treating cancer in a patient comprising intravenously administering to said patient a therapeutically effective amount of the pharmaceutical [formulation] *composition* of claim 30 diluted in a parenteral diluent.

44. The method of claim 43, wherein the one or more additional agents is an [H1 or H2] $H_1$ *or* $H_2$ antihistamine.

49. A method of treating cancer in a patient previously experiencing neurotoxicity comprising intravenously administering to said patient a therapeutically effective amount of the pharmaceutical [formulation] *composition* of claim 30 diluted in a parenteral diluent as a weekly infusion, wherein the total dose of the compound of formula I is less than about 200 mg/m².

52. A method of treating cancer while reducing or avoiding neurotoxicity which comprises intravenously administering a therapeutically effective amount of compound represented by formula I:

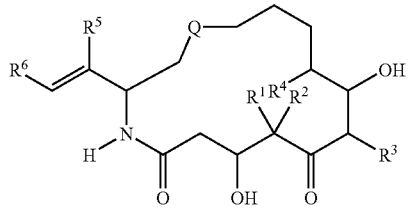

I wherein:

Q is selected from the group consisting of

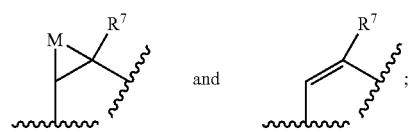

M is selected from the group consisting of oxygen, sulfur, $NR^8$ and $CR^9$, $R^{10}$, each $R^1$, $R^2$, $R^3$, $R^4$, $R^5$, $R^7$, $R^{11}$, $R^{12}$, $R^{13}$, $R^{14}$ and $R^{15}$ is, independently, selected from the group consisting of hydrogen, alkyl, substituted alkyl, aryl, substituted aryl and heterocyclo, and wherein [R'] $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$ and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any [salts,] solvates, or hydrates thereof;

over a period of one (1) hour to a patient in need thereof.

56. A method of treating cancer while reducing or avoiding neurotoxicity which comprises intravenously infusing a therapeutically effective amount of compound represented by formula [I] *II*:

II over a period of one (1) hour to a patient in need thereof.

58. A method of treating cancer in a human patient in need thereof with a synthetic or semi-synthetic epothilone [analogue] *analog* that is active against cancer which comprises a four (4) week dosing cycle wherein said cycle comprises three weeks of weekly intravenous administration and one week of oral administration of said epothilone [analogue] *analog*.

78. The pharmaceutical preparation of claim 15, wherein the quantity of solvent is an amount such that when the solvent is combined with the lyophilized epothilone *analog* the resulting solution contains from about 2 mg/mL to about 4 mg/mL of said analog.

79. A method of treating cancer in a patient comprising intravenously administering to said patient daily for 3 days or daily for 5 days a therapeutically effective amount of a compound represented by formula I:

I wherein:

Q is selected from the group consisting of and

;

M is selected from the group consisting of oxygen, sulfur, [NR] *NR⁸*, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ [,] is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any [salts,] solvates, or hydrates thereof.

82. The method of claim 81, wherein the compound of formula I is administered [in] *at* a dose of about 0.05 mg/kg to 200 mg/kg.

86. The method of claim 79, wherein the IV infusion is administered over a [perioe] *period* of about 1 hour.

88. The method of claim 86, wherein the one or more additional therapeutic agents is an [H¹, or H²,] *H₁ or H₂* antihistamine.

93. A method of treating cancer in a patient comprising intravenously administering to said patient every week or every 3 weeks a therapeutically effective amount of a compound represented by formula I:

I wherein:

Q is selected from the group consisting of and

;

M is selected from the group consisting of oxygen, sulfur, [NR] *NR⁸*, and $CR^9R^{10}$;

each $R^1$, $R^2$, $R^3$, $R^4$, $R^5$, $R^7$, $R^{11}$, $R^{12}$, $R^{13}$, $R^{14}$, and $R^{15}$ [,] is, independently, selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$; and each $R^9$ and $R^{10}$ is, independently, selected from the group consisting of hydrogen, halogen, alkyl, substituted alkyl, aryl, heterocyclo, hydroxy, $R^{14}C=O$, and $R^{15}OC=O$;

and any [salts,] solvates, or hydrates thereof.

94. The method of *claim* 93, wherein the compound of formula I is administered every week.

95. The method of *claim* 93, wherein the compound of formula I is administered every 3 weeks.

101. The method of claim 100, wherein the one or more additional therapeutic agents is an [H¹, or H²,] *H₁ or H₂* antihistamine.

106. The method of claim 95, wherein the compound of formula I is:

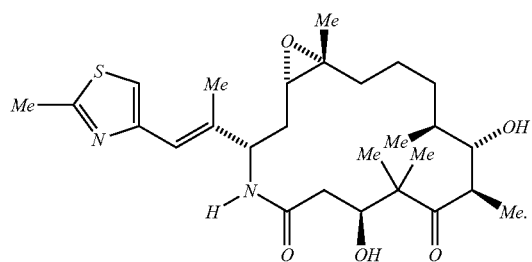

107. The method of claim 106, wherein the compound of formula I is administered in a dose of about 0.05 mg/kg to 200 mg/kg.

108. The method of claim 107, wherein the compound of formula I is administered over a period of about 10 minutes to about 3 hours.

109. The method of claim 107, wherein the compound of formula I is administered in a dose of about 30 mg/kg to 65 mg/kg.

110. The method of claim 109, wherein the compound of formula I is administered over a period of about 3 hours.

* * * * *